(12) United States Patent
Svatkova Hoeven et al.

(10) Patent No.: US 10,071,278 B2
(45) Date of Patent: *Sep. 11, 2018

(54) SYSTEMS FOR SIMULTANEOUSLY CONTRACTING BODY CORE MUSCLES AND A COMPUTERISED INSTRUCTIONAL UNIT FOR FACILITATING SAME

(71) Applicant: Core 46 IP, LLC, Irvine, CA (US)

(72) Inventors: M. Arnold Svatkova Hoeven, Tustin, CA (US); Jeremiah Hartzell, Irvine, CA (US)

(73) Assignee: Core 46 IP, LLC, Irvine, CA (US)

( * ) Notice: Subject to any disclaimer, the term of this patent is extended or adjusted under 35 U.S.C. 154(b) by 151 days.

This patent is subject to a terminal disclaimer.

(21) Appl. No.: 14/272,392

(22) Filed: May 7, 2014

(65) Prior Publication Data

US 2014/0243153 A1   Aug. 28, 2014

Related U.S. Application Data

(60) Continuation of application No. 14/049,071, filed on Oct. 8, 2013, now abandoned, which is a continuation (Continued)

(51) Int. Cl.
*A63B 15/02* (2006.01)
*A63B 71/00* (2006.01)

(Continued)

(52) U.S. Cl.
CPC ......... *A63B 23/0205* (2013.01); *A61H 1/005* (2013.01); *A63B 21/00061* (2013.01);

(Continued)

(58) Field of Classification Search
USPC .............................................. 482/1, 140–142
See application file for complete search history.

(56) References Cited

U.S. PATENT DOCUMENTS

| 4,807,873 A | 2/1989 | Naquin |
| 4,848,740 A | 7/1989 | van der Hoeven |

(Continued)

FOREIGN PATENT DOCUMENTS

| CN | 2 323 819 | 6/1999 |
| DE | 299 22 678 | 5/2000 |

(Continued)

OTHER PUBLICATIONS

Supplementary European Search Report for EP 08868072.3, dated Dec. 4, 2012.

(Continued)

*Primary Examiner* — Sundhara Ganesan
*Assistant Examiner* — Shila Jalalzadeh Abyan
(74) *Attorney, Agent, or Firm* — Morrison & Foerster LLP

(57) ABSTRACT

An exercise apparatus for exercising muscles of a user comprising a main body, an abdominal crunch exercise member pivotally attached to the main body, the abdominal crunch member configured to engage an upper body area of a user, an abdominal contact member attached to the main body, the abdominal contact member configured to engage an abdominal area of user; and an electronic vibration unit capable of causing a portion of the apparatus to vibrate.

12 Claims, 19 Drawing Sheets

1. Pull
(Medicine Ball and Row Machine)

2. Crunch
(AB Crunch Machine)

Related U.S. Application Data of application No. 13/049,706, filed on Mar. 16, 2011, now Pat. No. 8,550,966, which is a division of application No. 12/340,583, filed on Dec. 19, 2008, now Pat. No. 7,909,736.

(60) Provisional application No. 61/015,607, filed on Dec. 20, 2007.

(51) Int. Cl.

| | | |
|---|---|---|
| *A63B 21/00* | (2006.01) | |
| *A63B 23/02* | (2006.01) | |
| *A61H 1/00* | (2006.01) | |
| *A63B 24/00* | (2006.01) | |
| *G06F 19/00* | (2018.01) | |
| *A63B 21/06* | (2006.01) | |
| *A63B 71/06* | (2006.01) | |
| *A63B 21/008* | (2006.01) | |
| *A63B 21/055* | (2006.01) | |

(52) U.S. Cl.
CPC .... *A63B 21/00196* (2013.01); *A63B 23/0211* (2013.01); *A63B 23/0244* (2013.01); *A63B 24/0075* (2013.01); *G06F 19/3481* (2013.01); *A63B 21/008* (2013.01); *A63B 21/0552* (2013.01); *A63B 21/06* (2013.01); *A63B 23/0233* (2013.01); *A63B 2024/0081* (2013.01); *A63B 2071/063* (2013.01); *A63B 2071/0655* (2013.01); *A63B 2071/0658* (2013.01); *A63B 2208/0233* (2013.01); *A63B 2210/50* (2013.01); *A63B 2225/15* (2013.01); *A63B 2225/20* (2013.01)

(56) References Cited

U.S. PATENT DOCUMENTS

| | | | |
|---|---|---|---|
| 4,966,363 A | | 10/1990 | van der Hoeven |
| 5,005,832 A | | 4/1991 | van der Hoeven |
| 5,085,429 A | * | 2/1992 | Van Der Hoeven .......... 482/130 |
| 5,269,738 A | * | 12/1993 | Boren ................ A63B 23/0233 |
| | | | 482/100 |
| 5,304,107 A | * | 4/1994 | Jones ............................. 482/98 |
| 5,507,712 A | | 4/1996 | Chang |
| 5,556,363 A | * | 9/1996 | Hutchins ....................... 482/101 |
| 5,575,765 A | * | 11/1996 | Foster ....................... A61F 5/04 |
| | | | 602/32 |
| 5,651,755 A | | 7/1997 | Chen |
| D382,318 S | | 8/1997 | Hollinger |
| 5,669,863 A | | 9/1997 | Ho |
| D386,225 S | | 11/1997 | Chen |
| D387,401 S | | 12/1997 | Huang |
| 5,697,873 A | | 12/1997 | Straaten |
| 5,730,687 A | | 3/1998 | Ledany |
| 5,795,275 A | | 8/1998 | Van Der Hoeven et al. |
| 5,820,535 A | | 10/1998 | Van Der Hoeven et al. |
| 5,964,685 A | | 10/1999 | Boland |
| 6,053,851 A | | 4/2000 | Tu |
| 6,056,676 A | | 5/2000 | Adams |
| 6,206,811 B1 | | 3/2001 | Lat |
| 6,254,517 B1 | | 7/2001 | Kennedy |
| 6,626,808 B1 | | 9/2003 | Adams |
| 6,645,128 B1 | | 11/2003 | Hur |
| 6,694,550 B2 | | 2/2004 | Lee |
| 6,712,742 B2 | | 3/2004 | Suiter |
| 6,939,277 B2 | | 9/2005 | Tuller |
| 7,008,356 B2 | | 3/2006 | Hung |
| 7,101,328 B2 | | 9/2006 | Chiu |
| 7,267,641 B2 | | 9/2007 | Hsieh |
| D563,491 S | | 3/2008 | Kaplan |
| 2002/0011252 A1 | | 1/2002 | Finocchiaro et al. |
| 2002/0183177 A1 | * | 12/2002 | Hoffman .............. A61H 1/0218 |
| | | | 482/148 |
| 2004/0171466 A1 | | 9/2004 | Tuller |
| 2005/0032611 A1 | * | 2/2005 | Webber et al. ................ 482/72 |
| 2005/0124474 A1 | | 6/2005 | Van Der Hoeven |
| 2006/0073945 A1 | * | 4/2006 | Zuckerman .................... 482/56 |
| 2006/0234842 A1 | * | 10/2006 | Minami et al. ................. 482/99 |
| 2007/0265148 A1 | | 11/2007 | Lin |
| 2011/0275498 A1 | | 11/2011 | Brodess et al. |
| 2014/0243153 A1 | | 8/2014 | Hoeven et al. |

FOREIGN PATENT DOCUMENTS

| | | |
|---|---|---|
| WO | WO-94/02904 | 2/1994 |
| WO | WO-1994/009855 | 5/1994 |
| WO | WO-1999/032195 | 7/1999 |

OTHER PUBLICATIONS

International Search Report and Written Opinion for PCT/US17/14417, dated Jul. 5, 2017, 19 pages.

\* cited by examiner

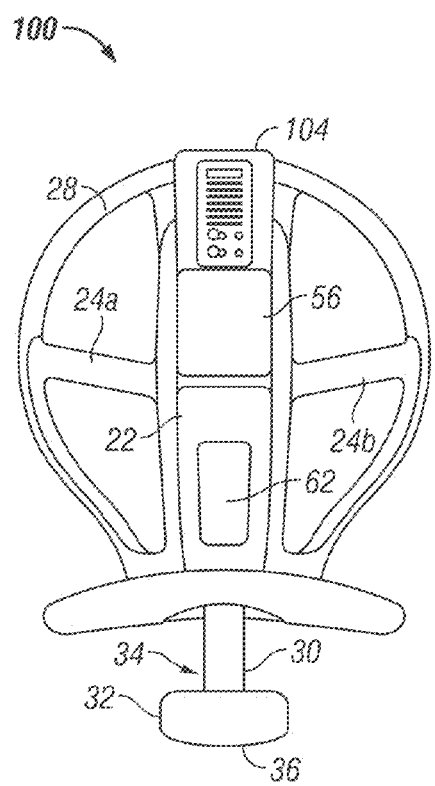
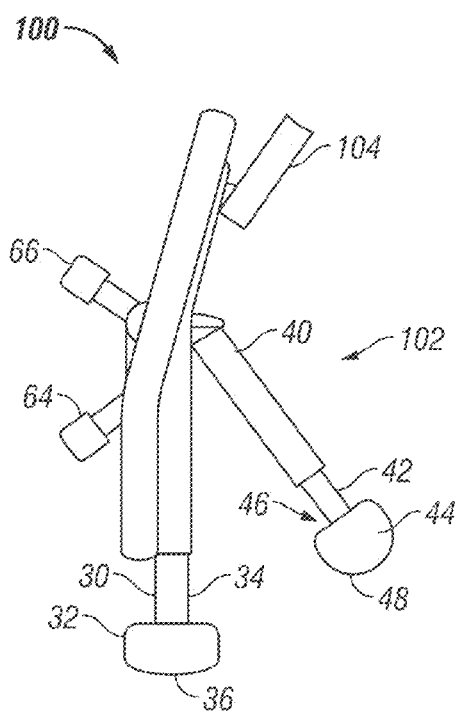
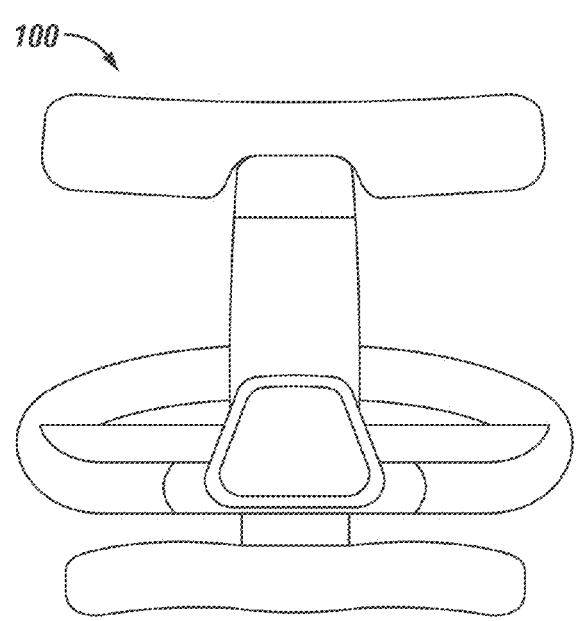
FIG. 2a
FIG. 2b
FIG. 2c

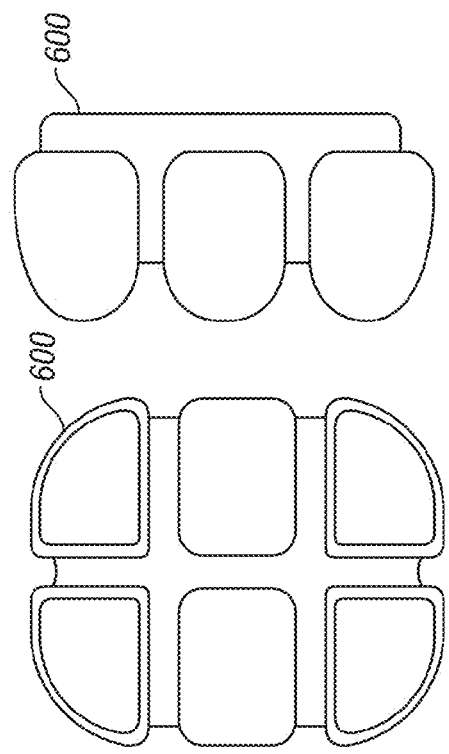
FIG. 6a
FIG. 6b
FIG. 6c
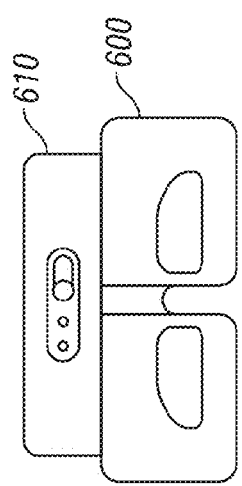
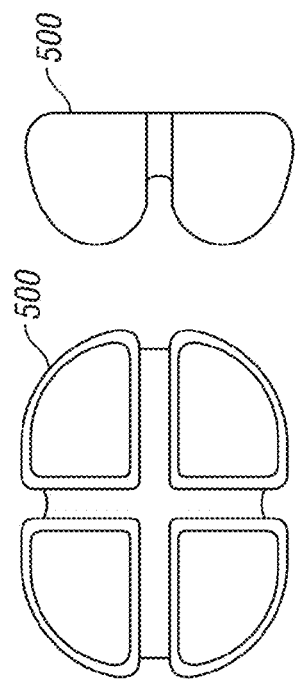
FIG. 5b
FIG. 5c
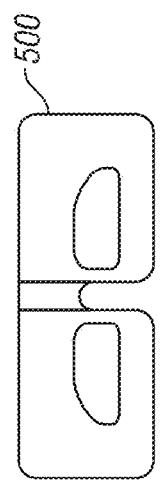
FIG. 5a 3. Hold
(All 3 Operations in One Exercise)

2. Crunch
(AB Crunch Machine)

1. Pull
(Medicine Ball and Row Machine)

3. Hold
(All 3 Operations in One Exercise)

2. Crunch
(AB Crunch Machine)

1. Pull
(Medicine Ball and Row Machine)

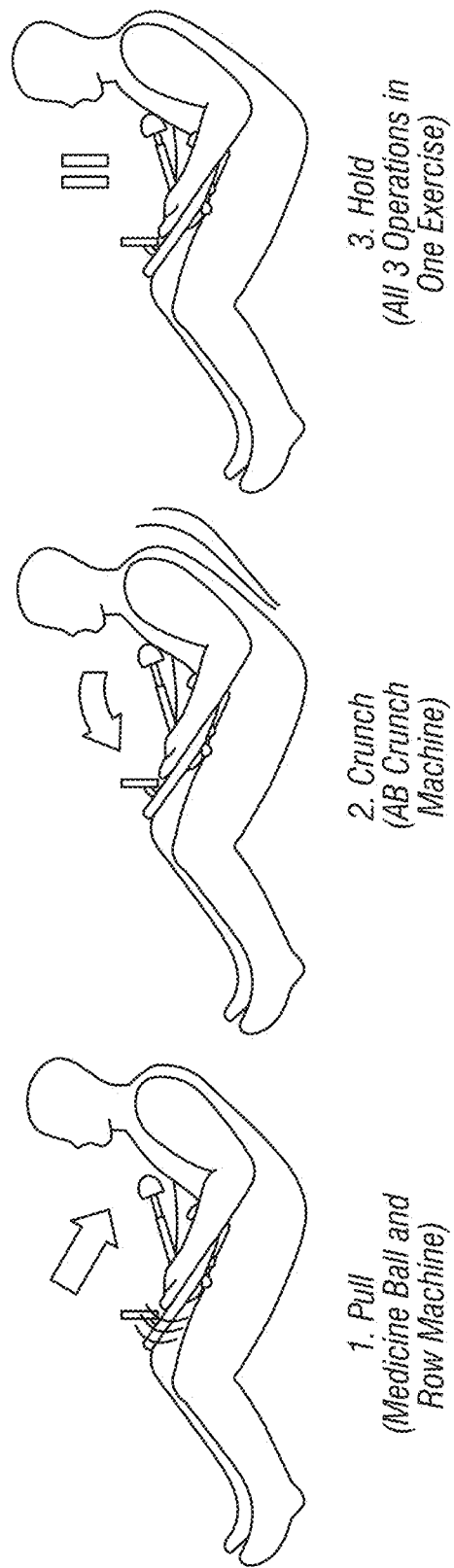

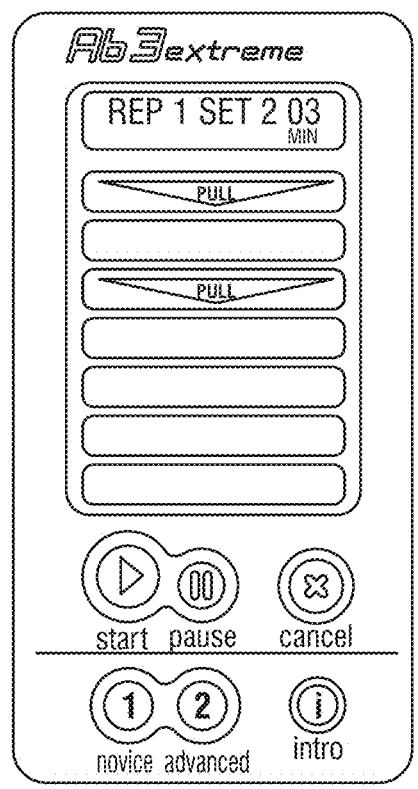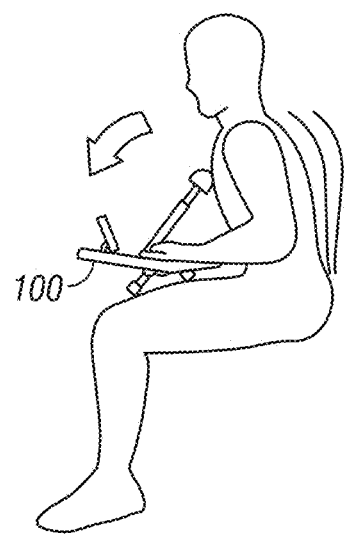
1. Pull
FIG. 11

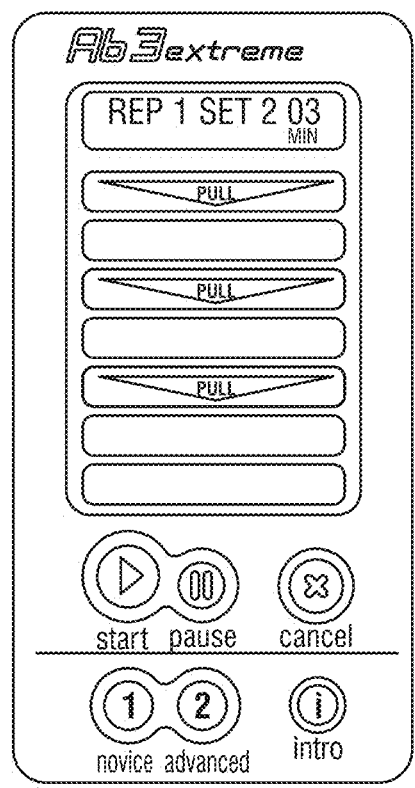
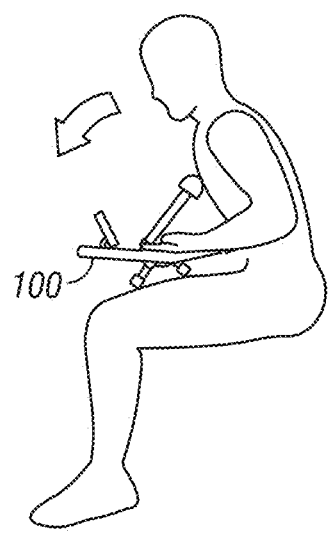
1. Pull
FIG. 12

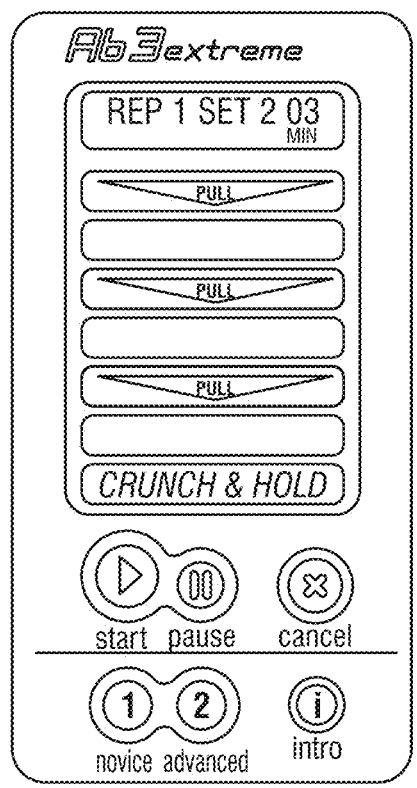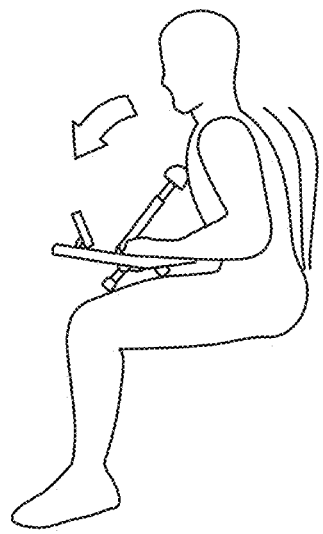
2. Crunch
*FIG. 13*

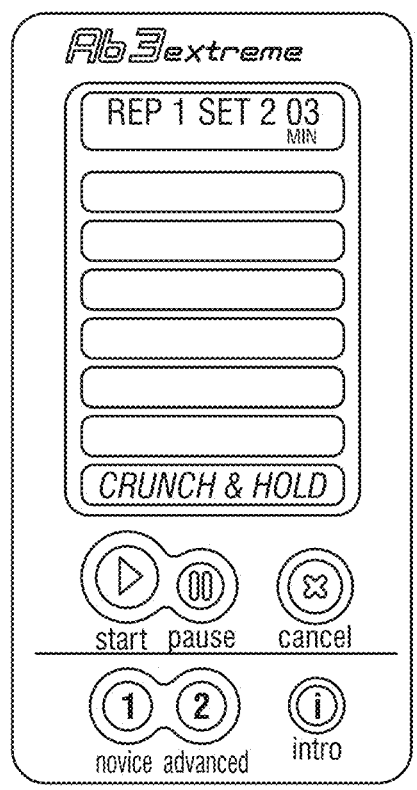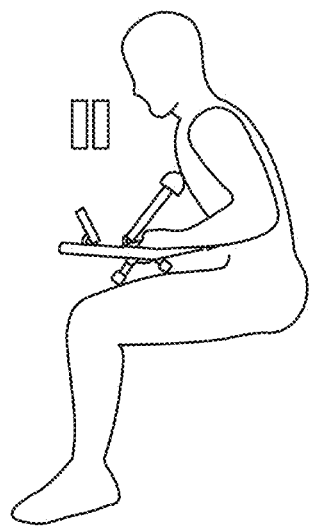
3. Hold
*FIG. 14*

SYSTEMS FOR SIMULTANEOUSLY CONTRACTING BODY CORE MUSCLES AND A COMPUTERISED INSTRUCTIONAL UNIT FOR FACILITATING SAME

CROSS REFERENCE TO RELATED APPLICATIONS

This application is a continuation of U.S. application Ser. No. 14/049,071, filed Oct. 8, 2013, which is a continuation of Ser. No. 13/049,706, filed Mar. 16, 2011, issued Oct. 8, 2013 as U.S. Pat. No. 8,550,966, which is a divisional of U.S. application Ser. No. 12/340,583, filed Dec. 19, 2008, issued Mar. 22, 2011 as U.S. Pat. No. 7,909,736, which claims benefit of priority under 35 U.S.C. § 119(e) to U.S. Provisional Patent Application No. 61/015,607, filed on Dec. 20, 2007, the contents of which are incorporated herein by reference in their entireties.

FIELD OF THE INVENTION

The present invention relates generally to gym, lower back physical therapy and home exercise devices. Some embodiments of the present invention relate to methods and devices for simultaneously exercising the core body muscles; specifically, contracting and isolating abdominal and back muscle groups. In addition, some embodiments can incorporate multiple resistances and exercises, which can be performed in one simultaneous action; guided by an electronic computerized instructional device.

BACKGROUND

Lower back pain annually costs the USA over $110 billion (doubling in the last 20 years) and is the second most common reason why an individual will see a doctor. One of the primary reasons for lower back pain is weak core muscles. Previously, there was no effective home core exercising devices that simultaneously isolates all core muscles in one simultaneous exercise motion.

An exercise method and device that can effectively strengthen all or many of 30 segmented core muscles, that is portable, effective, easy to use, and compact, and provides electronic instruction could provide many benefits. Exercising of the abdominal (also referred to as "Abdominal") and back musculatures can improve lower back stability, sports performance, posture and physical conditioning/appearance. Even sitting at a computer or desk a few hours a day, causes significant core strain. Strengthening the core can have a huge impact in the work place and lower back physical therapy. Typically, the first muscles to be activated in a sport, such as golf, running, basketball, tennis and etc; are the core muscles. Strengthening the core muscles can significantly increase body performance and reduces potential injury. Abdominal protrusion (allowing free forward movement of the body organs and waist fat) or "the pooch", can be due to weak core muscles, resulting in an unattractive appearance. Even though an individual is skinny, a pooch can many times not be eliminated by dieting alone. A solution can be strengthening the core muscles. The strengthening of the core muscles can provide an anatomical core girdle that can be more effective than any artificial girdle. Since fat has a low density, a strong core girdle can significantly reduce a forward protrusion around the waist.

There are nine abdominal muscle groups and each abdominal group can have a plurality of segmented muscles. For example, the rectus abdominis group (front body abdominals) has eight segmented muscles, the oblique's group (side abdominals) has twelve segmented muscles, and the serratus group has six segmented muscles. These muscles interconnect with the lats and back flexor muscles, collectively creating the core muscle group of 30 segmented muscles.

However, most abdominal exercise devices currently used in the home and gyms are single resistance apparatus that indirectly provide resistance to a single abdominal muscle group and without any emphasis on the back flexor and latissimus dorsi muscles. The total core is comprised of the front/side Abdominal groups, back flexor and latissimus dorsi muscles. Currently, there are no home exercise devices that simultaneously contract all core muscles in one single action; with minimal lower back movement. Moreover, if the abdominals are not contracted during the abdominal mechanical or non-mechanical exercise, the results are typically minimal. In addition, working core muscles separately can significantly reduce the intensity of the contractions and resistance of as oppose to multiple simultaneous contraction. Typically, the greater level of contraction of the core muscles, the higher level of fast twitch muscle fiber recruitment. This is why more resistance, less repetitions and slower anaerobic movements, can be more conducive to strengthening the core muscles. Fast twitch fibers provide anaerobic strength as opposed to slow twitch aerobic fibers that provide endurance. Many Abdominal/back machines incorporate fast movements resulting in very little strengthening of the Abdominal or and back fast twitch fiber muscles. As a result, an individual could be better off doing eighteen crunches slowly with a 30 pound medicine ball, as oppose to 300 crunches fast.

Furthermore, most abdominal exercise programs can require 5, 10 or even more different exercises in order to isolate all upper abdominal groups. Most gyms have four to seven different abdominal machines or abdominal slant boards. The process performing a number of exercises can take 20 to 60 minutes and involve extensive stress on the back and shoulder joints due to extensive movements required by many exercises and exercise devices. In addition, it can require the assistance of one or two trainers to perform some Abdominal exercises.

Anatomically, upper abdominal muscles differ from other muscles in the body like biceps or leg muscles, in two different ways.

First, abdominal or core muscles resist movement, whereas most other muscles propel a person. For this reason, contracting or tightening the abdominals during an exercise can be beneficial because doing so can cause muscle resistance. This can be conducive to muscles that resist as oppose to muscles that propel, resulting in further challenging of the muscle fibers or working out the muscle. Most individuals do not know how to properly tighten or contract their abdominals during crunch exercises, which can reduce their results by 70% to 80%. Muscles that resist typically need minimal movement to contract, whereas muscles that propel, like biceps, typically need a full range of movement. This is why many in the sports and academic community found abdominal crunches more effective over abdominal sit-ups. Seventy percent of the sit-up movement affected non-abdominal muscles, like the hip flexor muscles. Abdominal machines that incorporate extensive range of movement from twisting to bending have been found in scientific research journals to be ineffective or less effective than a crunch. An exercise and/or device that adds direct resistance to the abdominal muscles, comparable to the impact of a 30-50 pound abdominal medicine ball commonly used by professional boxers, during a crunch movement can beneficially result in a person contracting and tightening their abdominal muscles.

Secondly, the development of abdominal muscles can be difficult due to their non-jointed action. In comparison, jointed attached muscles like biceps are easier to contract: by simply moving the elbow joint. The abdominal muscles are not attached directly to any specific joint. This is why abdominal exercises with extensive joint movement can be inefficient and ineffective. In order to overcome this anatomical obstacle, an abdominal device is needed that can activate muscle groups that are inter-connected to abdominal muscles. Two specific examples of such muscles are the latissimus dorsi (attached to the side serratus abdominal muscles which connect to the front abdominals) and the back flexor muscles (attached to the anterior spine, which includes the abdominals; enabling flexing and arching of lower back). By contracting or activating the latissimus dorsi and back muscles, side and front abdominals can be indirectly activated.

The abdominal muscles can be comprised mainly of both slow and fast twitch fibers. Fast twitch fibers (as opposed to the slow twitch, endurance type ones), are composed of muscle fibers that provide strength and are thus designed for short exercise sessions with simultaneous explosion of extensive resistance and high intensity (anaerobic or non-cardio). In contrast, slow twitch fibers are typically adapted to provide endurance. Properly exercising slow twitch muscles can require long exercise sessions and low muscle intensity (aerobic or cardio). Because of these differences between types of muscles, fast-twitch fibers can respond best to heavy resistances and low repetition, in order to obtain muscular strength and development. Therefore, many individuals performing 50 to 100s of crunches, or using other abdominal exercises or machines that incorporate minimal resistance and extensive body movement per set (fast movements), can result in more cardio as oppose to muscle strength. As such, an object of a new abdominal machine can be to isolate the fast twitch fibers, in the shortest time frame, incorporating the highest level of multiple intensity and resistance.

What is needed is an improved abdominal exercise apparatus. Such an apparatus can include one or more of the following attributes:

(1) An apparatus that can simultaneously contract many or all twenty-four segmented abdominal muscles (within the rectus, oblique and serratus groups), lats and back flexox muscles, collectively constituting the core muscle groups. This could eliminate the need to use multiple different abdominal/back machines and/or abdominal/back exercises commonly used today. This type of apparatus could simultaneously contract many or all body core muscles, using multiple exercises and resistance in one device so that several exercises can be performed simultaneously.

(2) An apparatus that can incorporate multiple, adjustable resistance units. Each resistance unit can be adjustable up to 150 pounds of resistance, for example. This can provide a high intensity exercise within a short time.

(3) An apparatus that can provide direct resistance to the front abdominals comparable to the use of a medicine abdominal ball. Since the abdominal muscle resists as opposed to propel, such an apparatus can promote abdominal contraction during exercise.

(4) An apparatus that can provide adjustable resistance to the side abs, lats and back flexor muscles.

(5) An apparatus that can provide adjustable resistance to the front abdominal crunch exercise.

(6) An apparatus that can incorporate an electronic computerized personal trainer. Such a trainer could aid a user in performing a new methodology and exercise design that the user has never before experienced. For example, the trainer could guide the user through the proper form and technique with proper or optimal time frames of the repetitions and sets.

SUMMARY OF EMBODIMENTS OF THE INVENTION

Responsive to the foregoing needs and other needs, some embodiments of the present invention can provide three core resistance exercises; implemented in one simultaneous movement. The first exercise can be direct resistance to the front abdominals comparable to an abdominal medicine ball, a second exercise can be an angular resistance crunch and the third can be a resistance lateral pull (sometimes also referred to as a "lateral row"). In one embodiment, a device can provide adjustable resistance for some or all of these three exercises. Adjustable resistance can be provided through use of resistance compartments with interchangeable bands, weights, tension bands, hydraulics and the like.

Accordingly, some embodiments can combine three core resistance exercises that can simultaneously exercise core muscles and upper body muscles.

Various embodiments can also include an electronic (audio and visual) personal trainer that assists in the technique and training time of the exercise. The user can choose beginner or intermediate/advanced. The total time sessions can range from 3-4 minutes, for example. The user can chose four different positions depending on conditioning and ability. The home unit collapses into a collapsed, carrying configuration. In its operational mode, the unit unfolds.

One embodiment of an exercise apparatus can have a body forming a first yoke. The first yoke includes a first longitudinal channel extending therethrough and a first slide member is positioned in the first channel. The first slide member is slidable therein in a reciprocating manner and has an abdominal engagement end extending from the channel. The exercise apparatus can further include a second yoke pivotally attached to the body and has a second longitudinal channel extending therethrough. A second slide member is positioned in the second channel and is slidable therein in a reciprocating manner. The second slide member has an upper body engagement end extending from the second channel. The exercise apparatus can include a vibration unit operable to cause all or portions of the exercise apparatus to vibrate.

Another embodiment of the present invention is exercise apparatus for exercising muscles of a user having a main body and an abdominal crunch exercise member pivotally attached to the main body. The abdominal crunch member is biased to resist concentric motion thereof. The exercise apparatus also include a seat attached to the main body configured to support a user. The exercise apparatus also includes an electronic vibration unit functionally attached to main body and configured to induce vibrations through a user of the exercise apparatus.

BRIEF DESCRIPTION OF THE FIGURES

FIGS. 2a-2c are various views of the exercise device of FIGS. 1a-1d in an operational configuration.

FIGS. 5a-5c are various views of an exemplary "four pack" abdominal pad in accordance with various embodiment of the present invention.

FIGS. 6a-6c are various views of views of an exemplary "six pack" abdominal pad in accordance with various embodiment of the present invention.

FIGS. 9a-9c are schematic illustrations of using an exercise device in a hybrid seat/lying down position in accordance with various embodiment of the present invention.

FIGS. 10-17 illustrate use of an electronic coaching device in accordance with various embodiment of the present invention.

DESCRIPTION OF EMBODIMENTS OF THE PRESENT INVENTION

In the following description of preferred embodiments, reference is made to the accompanying drawings which form a part hereof, and in which it is shown by way of illustration specific embodiments in which the invention can be practiced. It is to be understood that other embodiments can be used and structural changes can be made without departing from the scope of the embodiments of this invention.

When simultaneously performing three abdominal exercises at one time, twenty-six abdominal muscles, the latissimus dorsi, arms and back muscles can be collectively contracted, which can result in a total core and upper body workout in less than four minutes. Mechanical and methodical processes of embodiments of the present invention can provide proper body positioning, resistance and multiple muscle isolation to contend with the complexity of the abdominal and back muscle groups. The attached drawings and diagrams provide a description of embodiments of the present invention.

Figure 3:
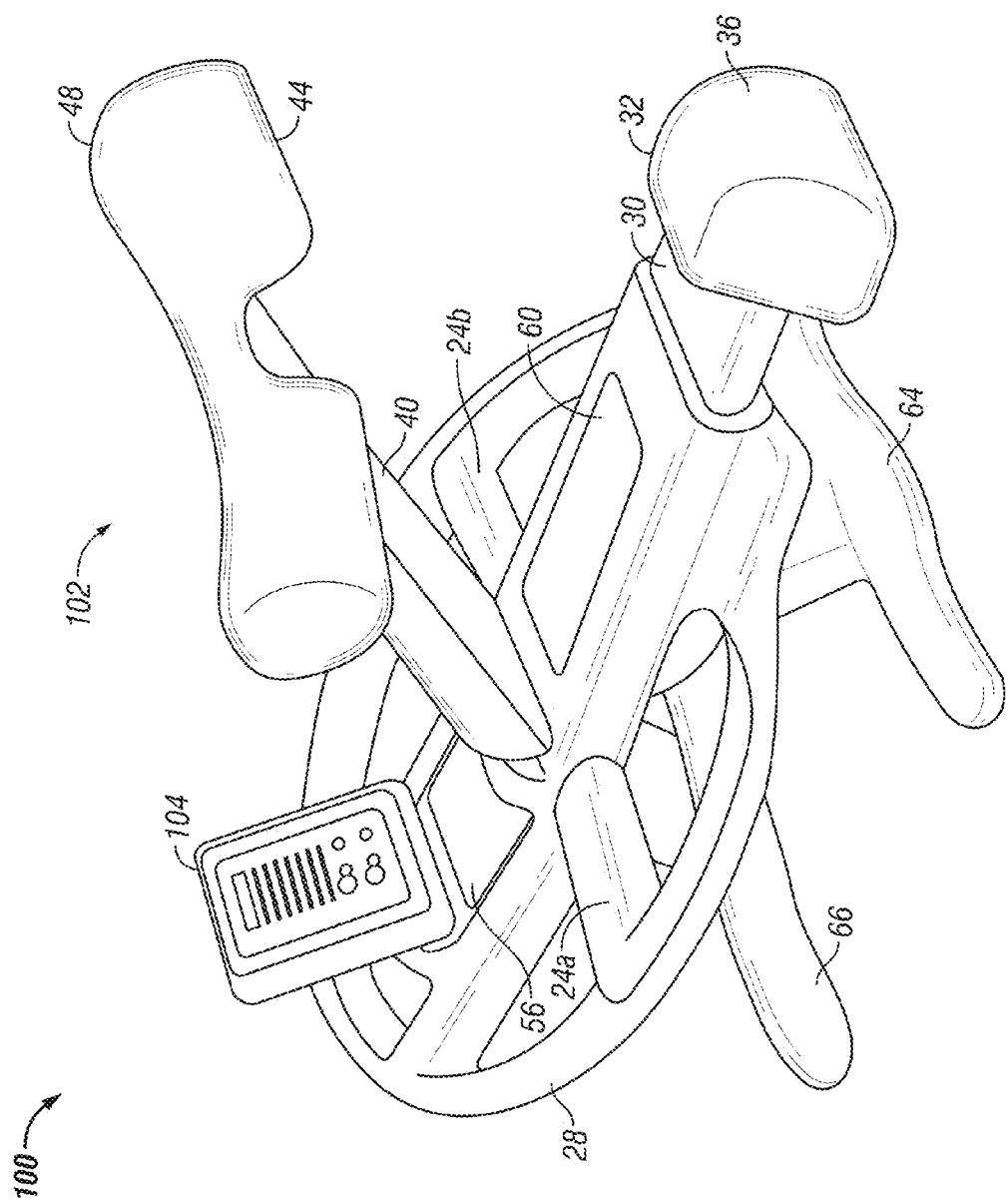
FIG. 3 is a perspective view of the exercise device of FIGS. 2a-2c.

FIGS. 1-3 illustrate an exemplary embodiment of a portable, home unit abdominal exercise device 100. FIGS. 1a-1d shows the device 100 in a compact, folded configuration and FIGS. 2a-2c shows the device 100 in an unfolded, operational configuration. FIG. 3 is a perspective view of the device in an operational configuration.

Figure 1A:
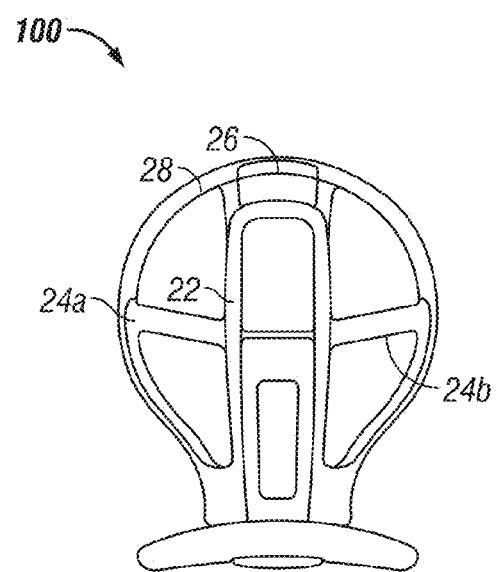
FIGS. 1a-1d are various views of an exercise device in a folded configuration in accordance with various embodiment of the present invention.
Figure 1B:
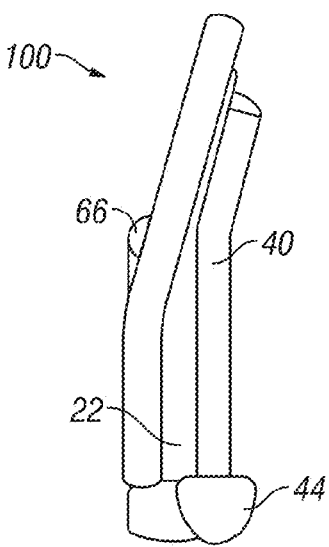
Figure 1C:
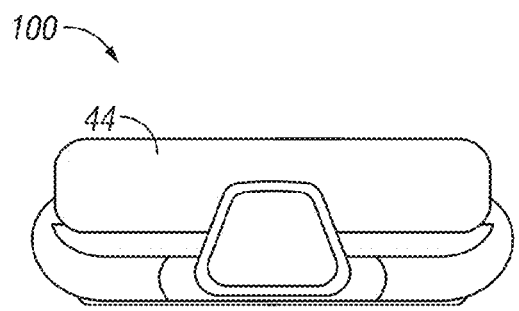
Figure 1D:
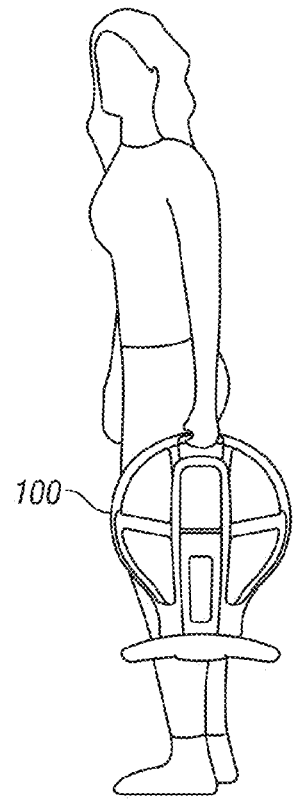

With reference to FIGS. 1a and 2a, the exercise device 100 can comprise a generally rectangular body 22 forming a first yoke that connects a pair of hand grips 24a and 24b. The hand grips can be positioned on opposing locations of the first yoke 22 and extend away from the yoke at angles with the X axis and Y axis. A substantially circular-shaped ring 28 can substantially encircle the body 22 and hand grips 24a and 24b. A carrying handle 26 (FIG. 1a) can be formed at one end of the ring 28 adapted for a user to grasp and carry the device 100, as shown in FIG. 1d.

With reference to FIGS. 2a and 2b, a first slide member 30 can be slidably held in a channel (not shown) that can extend through the center of the yoke of the body 22 in a direction defining a y-axis and substantially or completely perpendicular to an x-axis. The first slide 30 can reciprocate back and forth in a longitudinal direction in the channel. A first base 32 can be detachably connected at a first engagement end 34 of the first slide 30. The first engagement end 34 can extend out of the channel to engage a targeted muscle area, such as an abdominal muscle area of a user. The first base 32 (also referred to herein as an "abdominal pad") can have a first engagement surface 36, which can sized to provide a large contact area with a user's body to increase stability and reduce the pressure in the contact area. The base 32 can also be provided with a foam pad to cushion the contact area.

In some embodiments, a second yoke 40 can extend at an angle away from the body 22 in the operational configuration, as shown in FIG. 2b. In the folded configuration, the second yoke 40 can be collapsed into the body 22 lying substantially parallel to the first yoke, as shown in FIGS. 1a and 1b. Further to FIG. 2b, a second slide member 42 can be slidably held in a channel (not shown) that can extend through the center of the second yoke 40. The yoke 40 can extend away from the body 22 in the range from 20 to 70 degrees and in one embodiment, the range is from 30 to 60 degrees. The second slide 42 can reciprocate back and forth in a longitudinal direction in the channel.

A second base 44 (which can also be referred to herein as a "chest pad" or "upper body pad") can be detachably connected at a second engagement end 46 of the second slide 42. The second engagement end 46 can extend out of the channel to engage a targeted muscle area. The base 44 can have a user engagement surface 48, which can be sized to provide a large contact area with a user's body to increase stability and reduce the pressure in the contact area. The engagement surface 48 can also be provided with a foam pad to cushion the contact area. The second base 44 can also swivel or pivot on the second slide 42 to accommodate the rotational motion of a user when performing a crunch. The yoke 40, slide 42 and base 44, together, can be considered part of an upper body resistance mechanism 102.

Figure 7C:
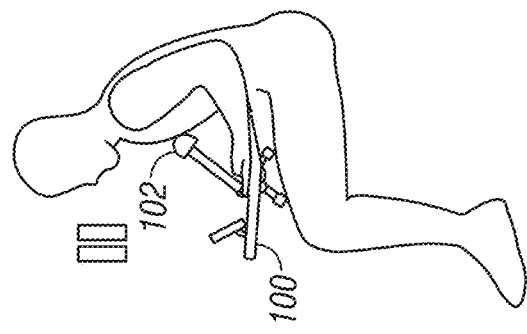
FIGS. 7a-7c are schematic illustrations of using an exercise device in a seated position in accordance with various embodiment of the present invention.
Figure 7B:
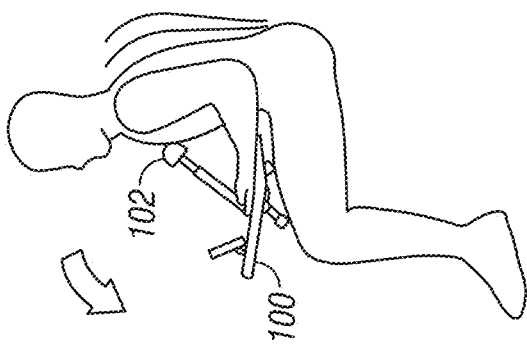
Figure 7A:
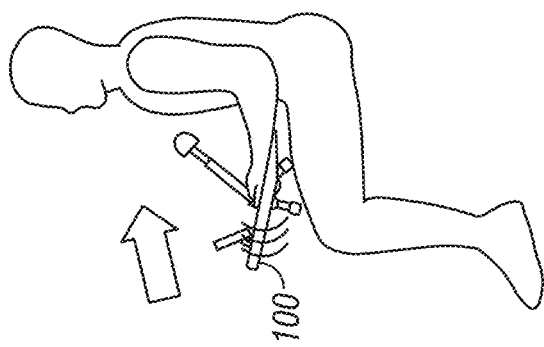

The body 22, hand grips 24a, 24b and ring 28 can be formed as an integral piece of plastic. The second yoke 40 can be pivotally connected at one end to a top portion of the body 22. In addition, a pair of leg supports 64 and 66 can be pivotally connected to a bottom portion of the body 22. In the folded configuration, the leg supports 64 and 66 can be folded into the body 22 to provide a low profile, as shown in FIG. 1b. In the unfolded configuration, the leg supports 64 and 66 can extend from the body and an angle, as shown in FIG. 2b. In operation, the leg supports 64 and 66 can rest on a users legs while the user is performing an exercise using the device 100, as shown in FIG. 7 for example.

The hand grips 24a and 24b can extend from the x-axis at equal angles, with the magnitude and direction of the angles selected such that the user's arms are placed in a natural position while exercising to increase stability. With the hand grips angled, the user's elbows can rest comfortably in a natural position besides the torso. To add further stability, the hand grips can extend at least as high, and preferably above, the top of the body 22 of the device 100.

With reference to FIG. 3, the body 22 can also include at least one cavity 56 centrally positioned in a lateral direction. The rectangular cavity 56 can be disposed so as to receive an electronic coach 104. The electronic coach 104 can be pivotally mounted at one end in the cavity so that it can be "popped up" out of the cavity 56 at an angle. Thus, the electronic coach 104 can conveniently extend out of the body of the device 100 in the operational configuration and can be collapsed into the cavity in the folded configuration shown, for example, in FIG. 1. Also, graphic and text instructions can be provided in a bottom surface (not shown) of the cavity 56 for providing specific instructions for the user when the coach 104 is in its operational configuration.

FIG. 3 provides a description of components of the abdominal device 100 in accordance with some embodiments. Use of certain components of the device 100 can be comparable to the biomechanical exercises performed with certain conventional gym exercise devices.

For example, a user pulling the hand grips 24a and 24b toward the user's body can correspond to an exercise traditionally performed on a row/lateral pull machine. When performing the lateral pull on the device 100, a user can hold the grips with palms facing up or down, which can exercise different muscles. Griping the hand grips 22 and 24 and pulling the hand grips 22 and 24 toward the user's body can be comparable to a row machine action, contracting and adding resistance to the side abdominals, laterals, back flexors and arms. Furthermore, the pad 32 and leg supports 64 and 66 can provide stability when performing this exercise.

Use of upper resistance mechanism 102 can correspond to use of an abdominal crunch exercise machine. In some embodiments, the resistance mechanism 102 can provide an angular line of motion, as opposed to a curved line of motion used in conventional abdominal machines. The upper pad 44 can be contoured the upper chest area of the human body and, in use, placed at the upper chest area of the user. The second yoke 40 can be adjustable, to accommodate user body types. In this manner, the second yoke 40 can be positioned at various angle with respect to the first yoke of the body 22 so as to accommodate different users. In other words, mechanical adjustments are provided that allow for height and/or length adjustments of various sizes and strength of particular individual users. In some embodiments, resistance to the various exercises can be adjusted using compartment 60, which contains various adjustable resistance mechanisms, including tension bands, cords, hydraulics, weights, etc.

Use of abdominal pad 32 positioned on a user's abdominal area can correspond to use of an abdominal medicine ball when the device is pulled toward the user in the lateral pull motion, described above. A conventional abdominal medicine ball can require an assistant to drop the ball, has no adjustable resistance and it provides impact resistance. In contrast, some embodiment of the device 100 can beneficially provide adjustable, direct resistance when a force is applied to the abdominal pad 32 into a user's abdominal area. Adjustable resistance can be provided through use of resistance compartment 62 with interchangeable bans, weights, tension bands, hydraulics and the like.

In addition, some embodiments simultaneously contract much, if not all, of the core muscles of a human body in one exercise motion. In use, and as illustrated in more detail in FIGS. 7-9, upper pad 44 can be placed on the front shoulders of a user, implementing a forward crunch, lower pad 32 can be placed between the middle and lower front abdominal area, and the user can grip the hand grips 24a and 24b with palms facing up or down.

Figure 4:
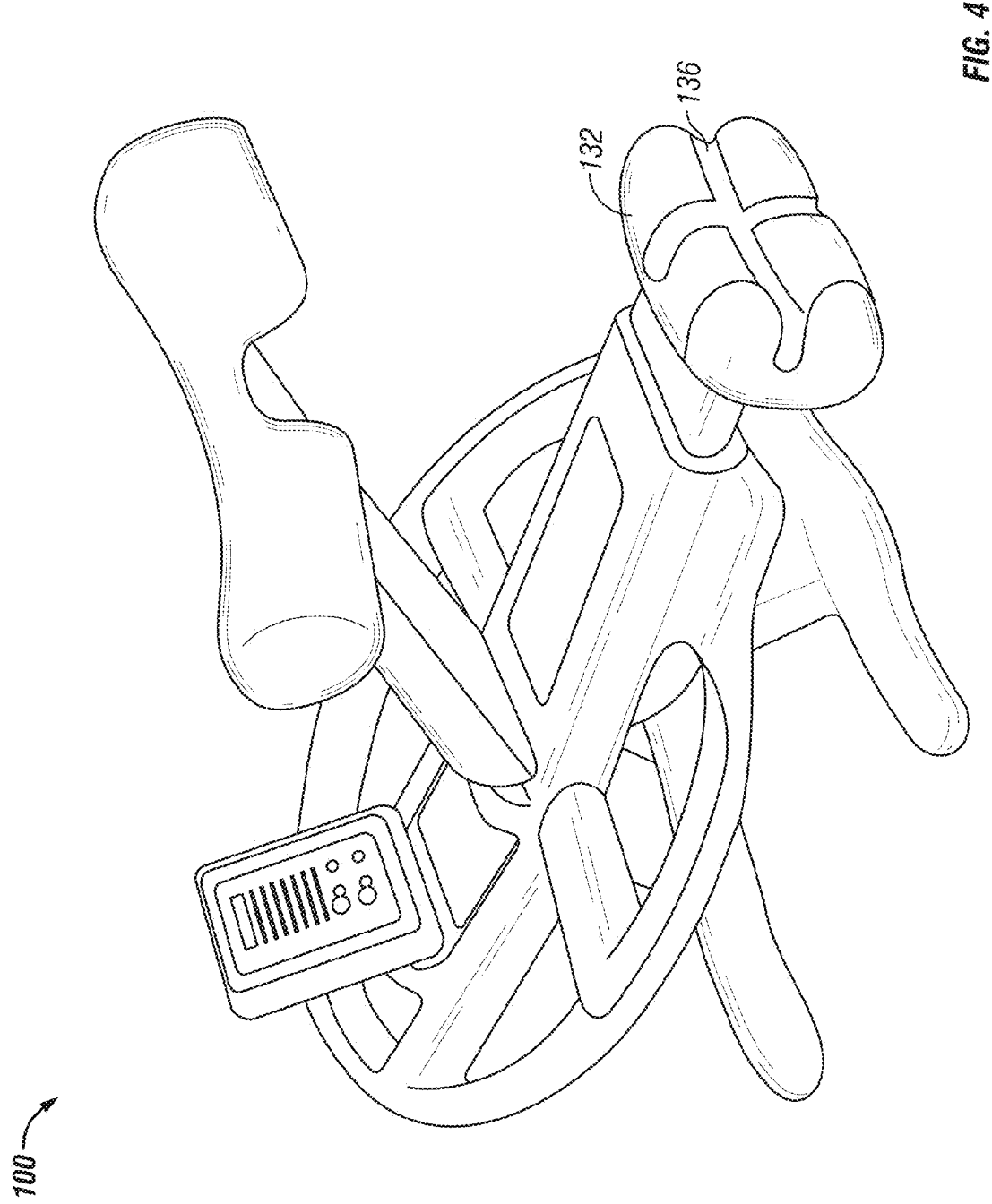
FIG. 4 is a perspective view of the exercise device of FIGS. 2a-2c with a different abdominal pad in accordance with various embodiment of the present invention.

As discussed above, leg pad supports 64 and 66 can be placed on the upper thighs of a user. The supports can be adjustable, based on a user's upper body height. An adjustment mechanism can allow for the adjustability, in a upward or downward direction. For example, in one embodiment, leg pad located at ends of the leg supports 64 and 66 can be cushioned and contoured to accommodate the thigh area of a user FIG. 4 illustrates the device 100 using a detachable four pack abdominal pad 132 instead of the single, more rounded abdominal pad 32 illustrated in FIG. 3. In one embodiment, the four pack abdominal pad 132 is designed to specifically isolate four segmented middle and lower frontal abdominal muscles. The pad segments can be designed with a radius of curvature to more closely contour to the shape of the human abdominal area.

FIGS. 5 and 6 illustrate various views of further embodiments of lower abdominal pads, including a "four pack" abdominal pad 500 (FIGS. 5a-5c) and a "six pack" abdominal pad 600 (FIGS. 6a-6c). In accordance with various embodiments of the present invention, an electronic vibration unit (not shown) may be added to the device 100, which can provide further benefits when performing abdominal exercises. As shown in FIG. 6, the six pack lower abdominal pad 600 includes a vibration unit 610, which can cause the abdominal pad 600 to vibrate when in use. It is understood that such a vibration unit can be incorporated with other types of abdominal pads described herein or in other portions of the device 100 to provide vibration explained above, and is not limited to use with only a lower abdominal pad. For example, the vibration 610 can cause other portions of the device 100 to vibrate, including the hand grips 24a and 24b and upper body pad 44. Furthermore, embodiments of the present invention need not be limited to a single vibration unit, as multiple, separate units can be used to cause various portions of the device 100 to vibrate.

Figure 8C:
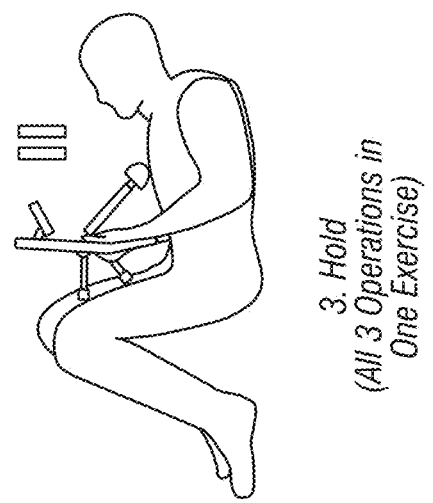
FIGS. 8a-8c are schematic illustrations of using an exercise device in a lying down position in accordance with various embodiment of the present invention.
Figure 8B:
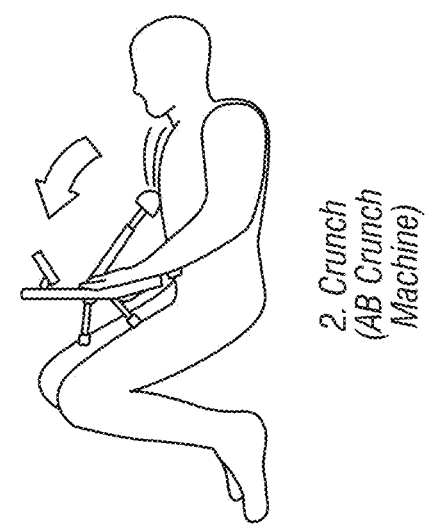
Figure 8A:
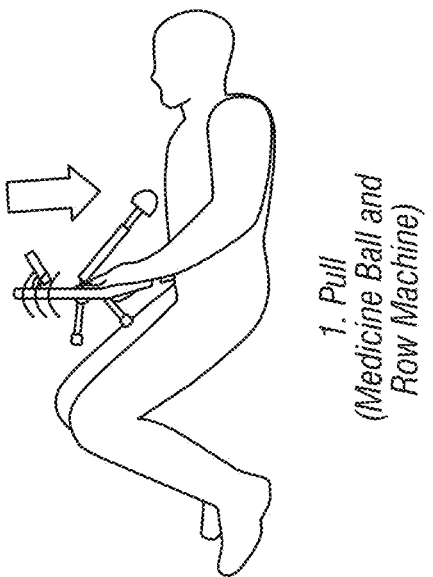
Figure 10:
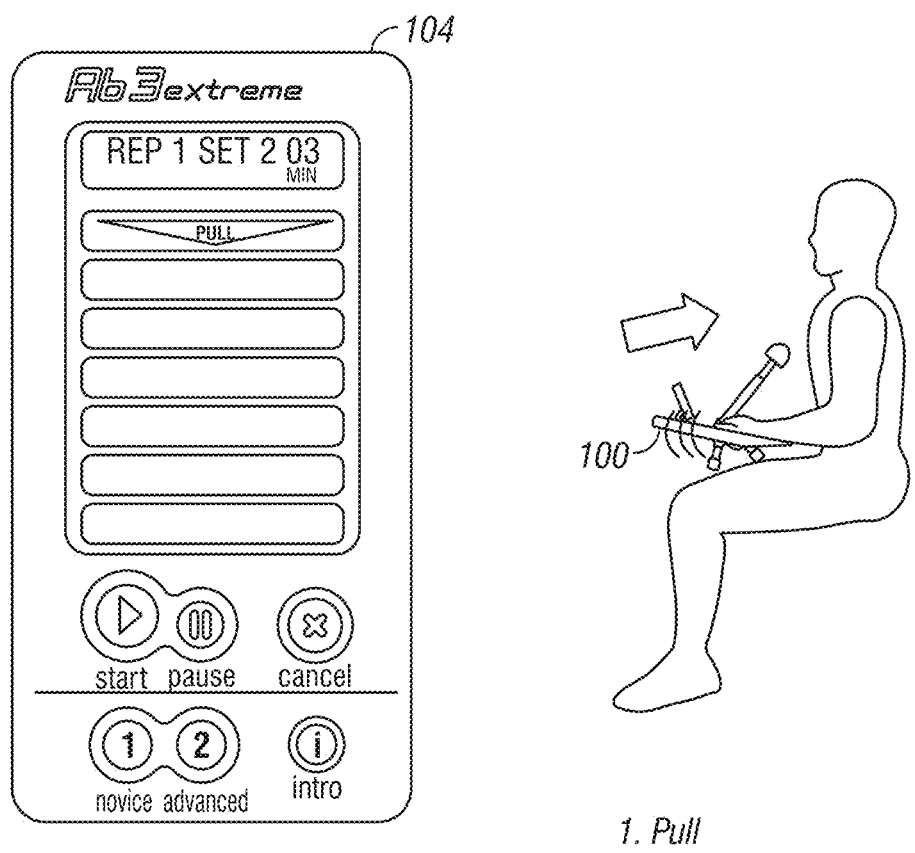
Figure 15:
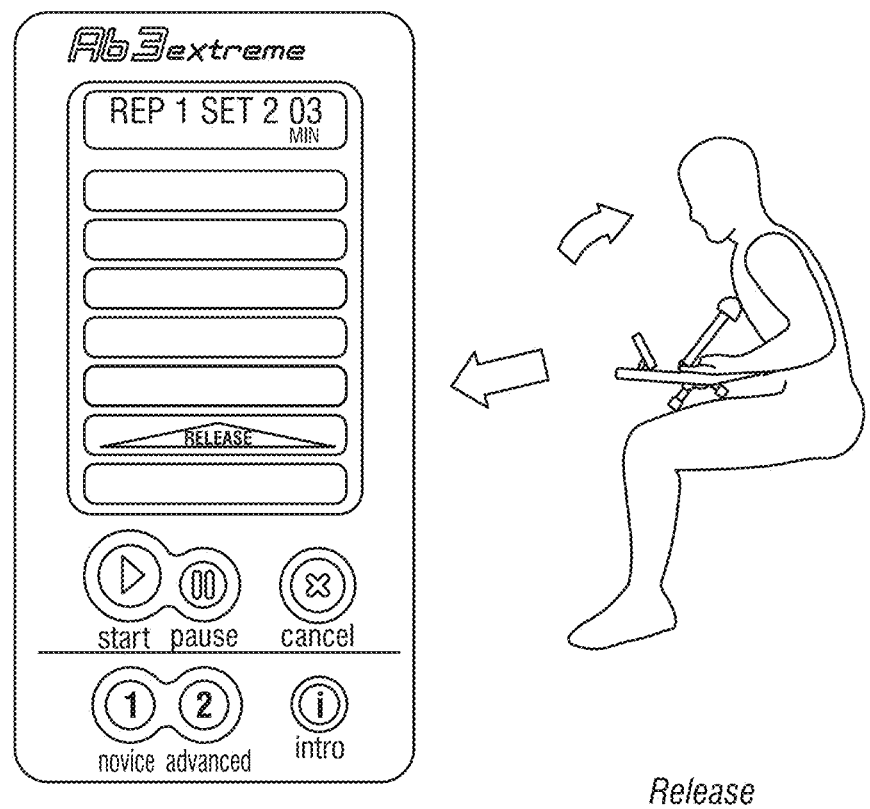
Figure 16:
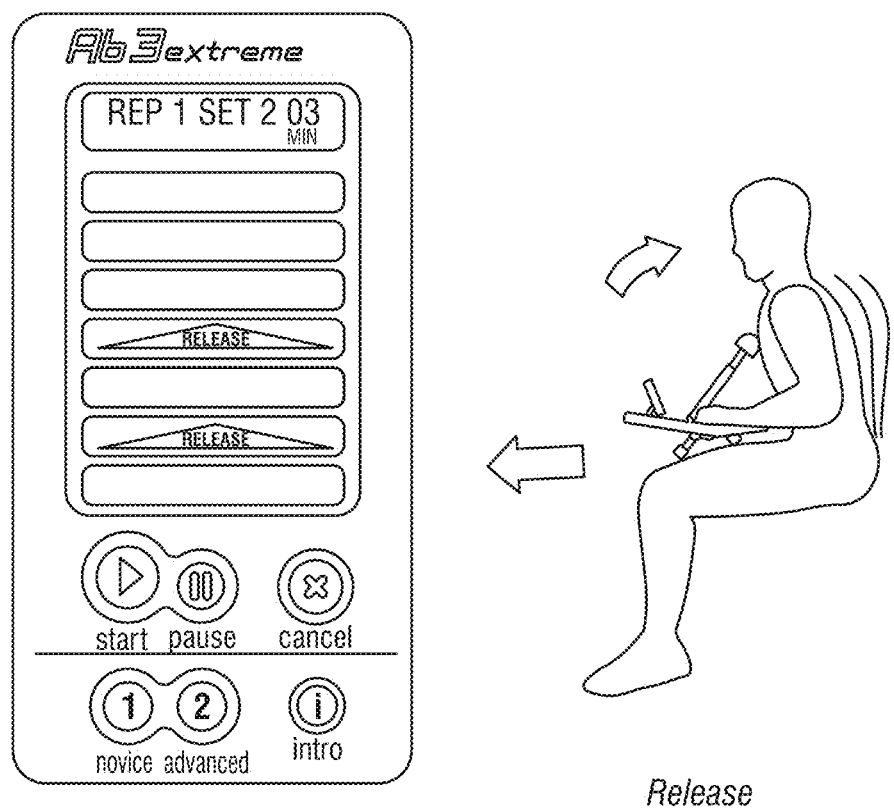
Figure 17:
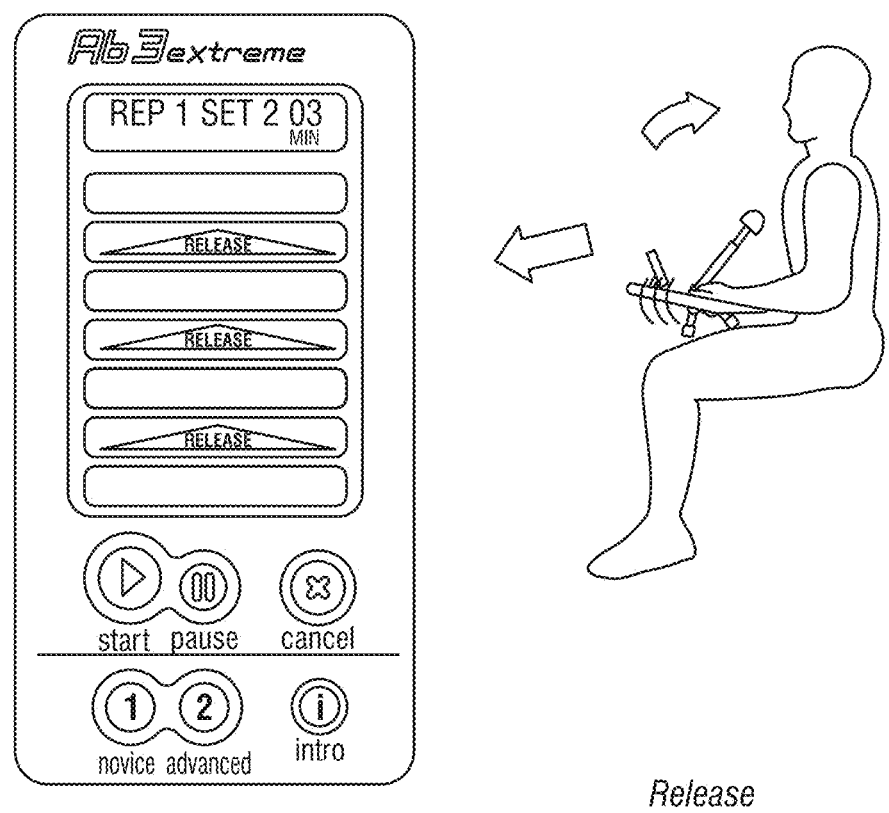

FIGS. 7-9 illustrate various methods of using the device 100 in accordance with exemplary embodiments of the present invention. The methods can obtain optimal contraction and high efficiency of use. FIGS. 7-9 illustrates use of the device 100 in a sitting position, FIGS. 8a-8c illustrates use of the device 100 in a lying down position, and FIGS. 9a-9c illustrates use of the device 100 in a hybrid sitting/lying down position.

The device 100 can be used by pulling the device 100 toward the user, with the user gripping the hand grips of the device 100 with his or her palms facing up. This can exercise the lower abs, middle abs, side abs, lats, back and arms. The user can alternatively grip the hand grips with palms facing down, which can exercise different muscles or the same muscles differently. For example, with palms facing down, the device may primarily exercise triceps and shoulder muscles.

The progressive action of pulling, crunching and holding, is a three action method that can isolate most or all core muscles. In addition, the device's pulling pressure on the frontal abdominals can prevent lordosis or curvature of the lower back. This can reduce pressure on the lower back, critical to individuals with low back pain. As discussed above, a user can perform a "crunch" by crunching against the upper pad 44. This can exercise the upper abs. It should also be noted that the figures illustrated the crunch motion in a rotational fashion; however, the crunch can also be performed at a straight angle. In other words, a user can push his or her chest so that the upper pad 44 moves straight into the body of the device 100, as discussed above.

In accordance with some embodiments, a user can perform a new methodology of exercising the core abdominal and back muscles, based on simultaneous use of multiple core exercises and resistance. This can be beneficial due to the core's multiple muscle configuration and its unique muscle action. The user's pull and crunch action can be a concentric or positive resistance movement. At this point, all three exercises can be activated. The user can then hold the device for an amount of time, such as 1 to 5 seconds, which can further exercise the upper, lower and middle abs, and back as well as the lats and arms. The user slowly release's the unit, resulting in an eccentric or negative resistance movement. The user can then relax and then repeat the above steps. The above steps need not be performed in the order described above, nor do all of the steps need to be performed sequentially. For example, one or more of the steps can be performed simultaneously, for example the crunch and pull steps can be performed at the same time.

In accordance with various embodiments, use of the device 100 in a sitting position (see FIGS. 7*a*-7*c*) can provide a beginner exercise, use of the device 100 in a lying down position (see FIGS. 8*a*-8*c*) can provide an intermediate exercise and use of the device in a hybrid sitting/laying down position (see FIGS. 9*a*-9*c*) can provide an advanced exercise.

FIGS. 10-17 illustrate use of the voice and visual electronic personal trainer 104 in accordance with an exemplary embodiment of the present invention. An exemplary electronic personal trainer is described in published U.S. Patent No. 2005/0124474 titled "Abdominal exerciser with Electronic Coaching Device," which is hereby incorporated by reference in its entirety. In general, the electronic personal trainer 104 can provide a user with instruction regarding how to perform exercise with the device 100. With the electronic personal trainer 100, a user can select between beginner and advanced workouts. Appropriate timing between repetitions, sets and periods of resting can be beneficial to isolate fast twitch muscles; especially muscles that resist. Embodiments of the present invention can be set to correspond to scientific optimal levels of timing and procedures.

A majority of individuals do not know the proper timing and process of abdominal tightening, breathing, sets, reps, optimal exercise time. Accordingly, embodiments of the present invention can provide introductory instructions and daily exercise operations. The user can also choose the level of ability. During operation of the unit, it can provide visual lighting and text, plus voice instruction. It would typically require two to three personal trainers to accomplish what the current electronic instructional unit can accomplish.

Various embodiments can include computer memory for storing information relating to a user's use of the device 100 over a specific period of time, for example. A computing device residing in the device 100, such as in the electronic coach or other computer device, can use the information stored in the computer memory to provide reporting of the use of the device 100, including displaying information in graphic form on a display of the computing device. The device 100 can also include an interface to connect the computer memory with a separate computer for transmitting information relating to the use of the device 100 to the separate computer.

With reference to FIGS. 10-17, in some embodiments, an electronic coach can aid the user in accomplishing a multiple muscular phase exercise activity by determining that a first muscular phase (e.g., a concentric phase) can be performed, and providing a user perceptible output that prompts and instructs the user how to properly perform this phase. The electronic coach can determine that a second muscular phase (e.g. an isometric phase, illustrated in FIG. 14) can be performed and provides a second user perceptible output that is different than the first, that prompts and instructs the user how to properly perform this phase. The electronic coach may then determine that a third muscular phase, the eccentric phase (illustrated in FIGS. 15-17), can be performed and then provides a third user perceptible output that is different than the first and second that prompts and instructs the user how to properly perform this phase. The electronic coach can instruct the user through both visual and audio outputs as to the proper timing and method of performing each phase of the exercise activity. In addition, a side or rear memory slot on the computerized trainer 400 can accept a memory card. The memory card can store data relating to the user's exercise performance, bio-data, usage and the like for later analysis by a physician or physical therapy professional, for example.

Figure 18:
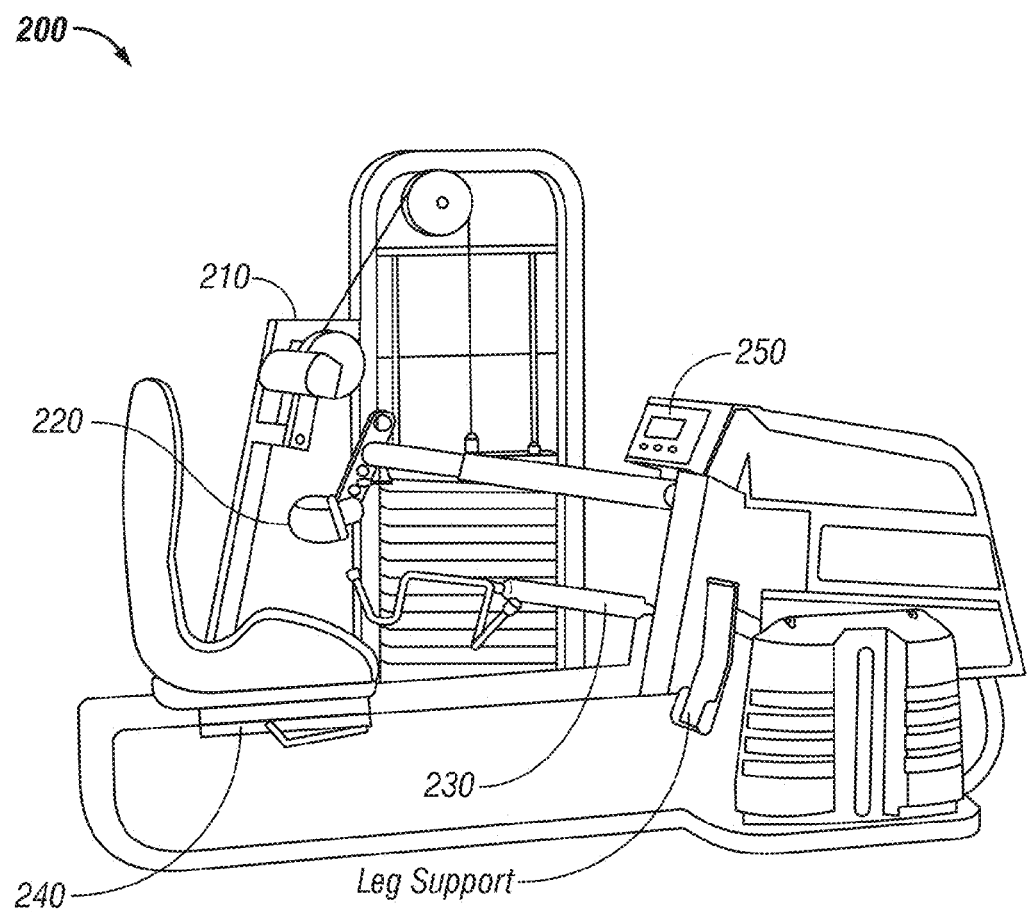
FIG. 18 illustrates an exemplary exercise machine in accordance with various embodiment of the present invention.

FIG. 18 illustrates a commercial abdominal exercise machine 200 in accordance with an exemplary embodiment of the present invention. The exercise machine can include a chest crunch mechanism 210, an abdominal pad mechanism 220, and a lateral row mechanism 230. The machine 200 can include a mechanical vibration unit 240 that causes a user to oscillate in three dimensions and is produced by two motors. The oscillating action can be combined with performing resistance exercises using embodiments of the present invention, such as device 100 and machine 200. Thus, embodiments of the present invention can combine three resistance core exercises with internal accelerated vibration. This can significantly increase core muscle development. One such vibration unit is commercially available as the Power-Plate® my5 from Power Plate North America, Inc., located in Northbrook, Ill. In one embodiment, the vibration unit 240 is located under a seat of the exercise machine 200 and causes the seat to vibrate, however, other portions of the exercise device can vibrate instead or in addition to the seat, such as the chest crunch mechanism 210, abdominal mechanism 220 and/or lateral row mechanism 230.

Figure 19:
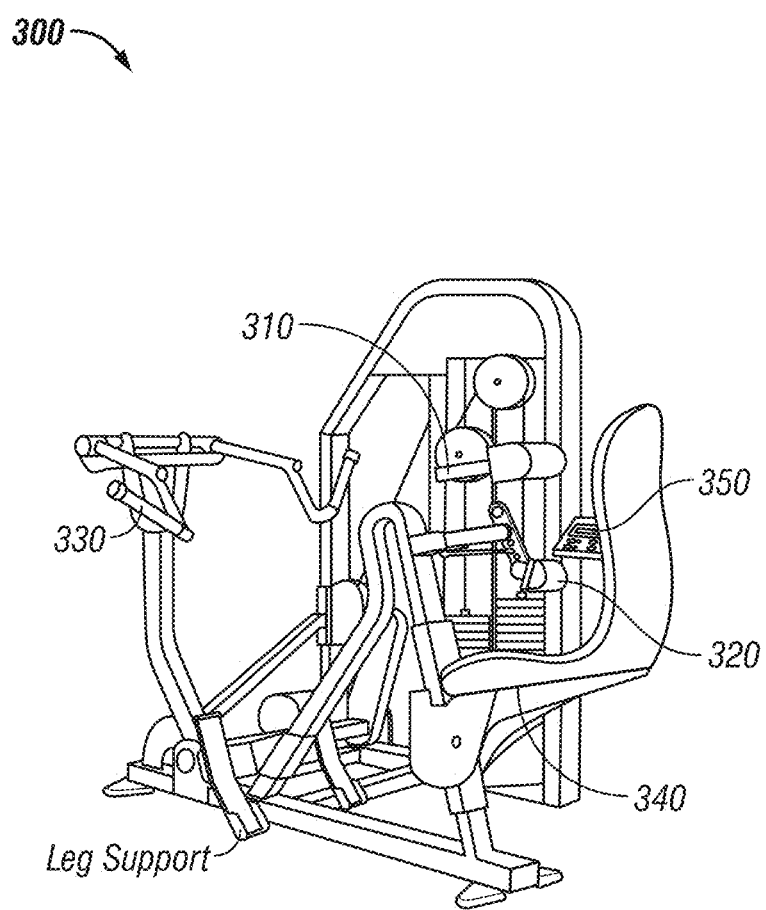
FIG. 19 illustrates a further exemplary exercise machine in accordance with various embodiment of the present invention.

FIG. 19 illustrates a further embodiment of an abdominal exercise machine 300 in accordance with the present invention. The abdominal exercise machine 300 has similar components to exercise machine 200, including a chest crunch mechanism 310, an abdominal mechanism 320, a lateral row mechanism 330 and vibration unit vibration unit 340. In addition, exercise machine 300 includes a user interface 350 that can incorporate the functions of the electronic coach unit described above. The interface 350 can also include controls for the vibration unit 340, such as turning the vibration off and on and the amount of vibration.

Figure 20:
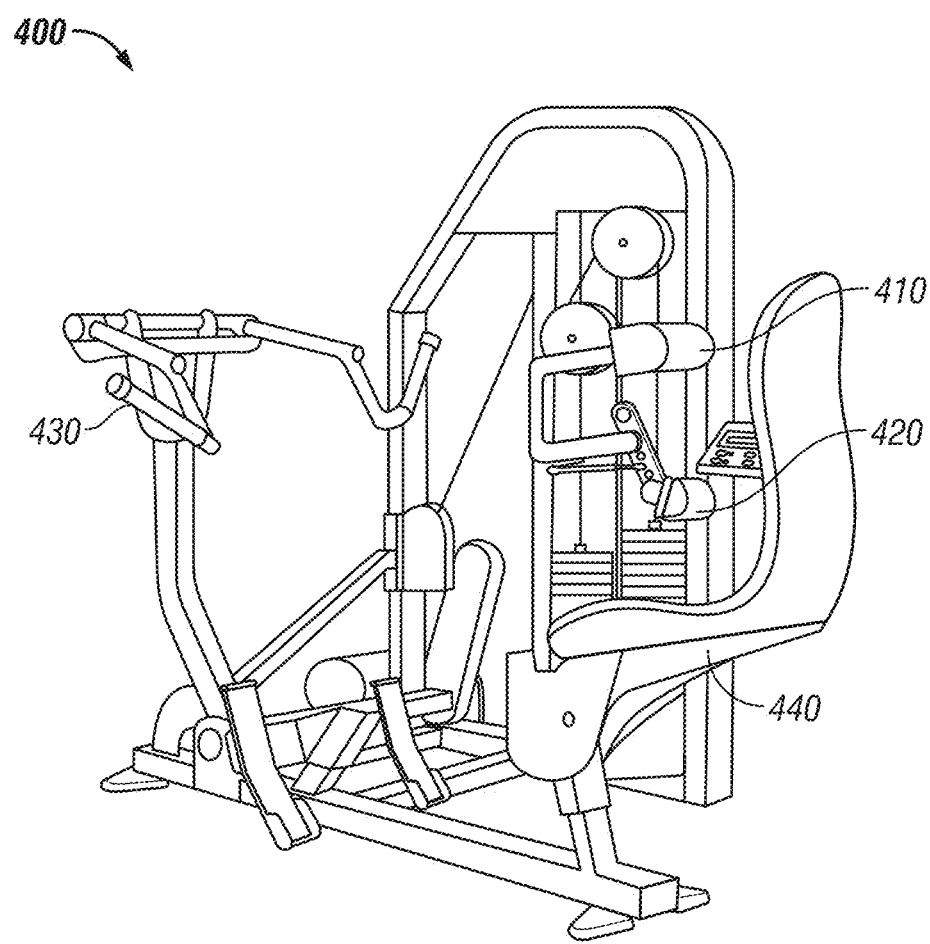
FIG. 20 illustrates yet a further exemplary exercise machine in accordance with various embodiment of the present invention.

FIG. 20 illustrates yet another embodiment of an abdominal exercise machine 400 in accordance with the present invention. Embodiment 400 is similar to embodiment 300, but with the crunch pad 410 directly connected to an abdominal pad 420.

Advantageously, use of embodiments of the abdominal devices disclosed herein can simultaneously contract many, if not all, of the various types of abdominal muscles. Thus, a user can exercise his or her abdominal muscles using a single machine in a shorter amount of time than with use of conventional machines.

It should also be noted that there are many alternative ways of implementing the methods and apparatuses of the present invention. It is therefore intended that claims eventually issuing from one or more patents claiming priority to the present application be interpreted as including all such alterations, permutations, and equivalents as fall within the true spirit and scope of the present invention.

What is claimed is:

1. An exercise apparatus for exercising muscles of a user comprising:
   a main body;
   an abdominal contact element connected to the main body, the abdominal contact element configured to provide resistance for a front abdominal contact exercise by contacting an abdominal region of the user;
   a chest contact element connected to the main body, the chest contact element configured to provide resistance for an abdominal crunch exercise by contacting a chest region of the user; and
   a lateral pull element connected to the main body, the lateral pull element configured to provide resistance for a lateral pull exercise, wherein the lateral pull exercise comprises both of the user's forearms and hands moving perpendicular to the torso in a direction from the user's chest to the user's back, wherein
   the apparatus is configured to enable the user to simultaneously perform the front abdominal contact exercise using the abdominal contact element, the abdominal crunch exercise using the chest contact element, and the lateral pull exercise using the lateral pull element, and wherein
   the apparatus is configured so that the abdominal contact element contacts the abdominal region of the user and the chest contact element contacts the chest region of the user when the user simultaneously performs the front abdominal contact exercise, the abdominal crunch exercise, and the lateral pull exercise.

2. The exercise apparatus of claim 1 further comprising a pair of leg supports connected to a portion of the main body opposite the chest contact element and configured to provide an opposing force to the chest contact element when the user simultaneously performs the front abdominal contact exercise, the abdominal crunch exercise, and the lateral pull exercise.

3. The exercise apparatus of claim 2, wherein the pair of leg supports are pivotally connected to the bottom portion of the main body.

4. The exercise apparatus of claim 2, wherein the pair of leg supports are configured to rest on the user's thighs while the front abdominal contact exercise, the abdominal crunch exercise, and the lateral pull exercise are performed simultaneously by the user.

5. The exercise apparatus of claim 1 further comprising an electronic coach.

6. The exercise apparatus of claim 5, wherein the electronic coach comprises computer memory for storing information relating to a user's use of the apparatus over a period of time.

7. The exercise apparatus of claim 1, wherein at least one of the chest contact element's resistance and the lateral pull element's resistance is adjustable.

8. The exercise apparatus of claim 1, wherein the chest contact element's resistance and the lateral pull element's resistance are adjustable.

9. The exercise apparatus of claim 1, wherein the abdominal crunch exercise is an angular abdominal crunch exercise.

10. The exercise apparatus of claim 1, wherein the apparatus is configured for the user to simultaneously contract twenty-six of the user's abdominal muscles, the user's latissimus dorsi, the user's arms, and the user's back muscles.

11. The exercise apparatus of claim 1, wherein the apparatus is configured to enable the user to be seated when the user simultaneously performs the front abdominal contact exercise, the abdominal crunch exercise, and the lateral pull exercise.

12. The exercise apparatus of claim 1, wherein the apparatus is configured so that the lateral pull element exerts a force on the abdominal contact element when the user simultaneously performs the front abdominal contact exercise, the abdominal crunch exercise, and the lateral pull exercise.

* * * * *